(12) United States Patent
Yamauchi

(10) Patent No.: US 9,195,045 B2
(45) Date of Patent: Nov. 24, 2015

(54) ENDOSCOPE APPARATUS HAVING FIRST AND SECOND LIGHT SOURCES AND CONTROL SECTION WHICH CONTROLS THE FIRST LIGHT AND SECOND LIGHT SOURCES ACCORDING TO A DETECTED TYPE OF ATTACHED ADAPTER

(71) Applicant: OLYMPUS CORPORATION, Shibuya-ku, Tokyo (JP)

(72) Inventor: Hideyoshi Yamauchi, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 74 days.

(21) Appl. No.: 14/034,133

(22) Filed: Sep. 23, 2013

(65) Prior Publication Data

US 2014/0355289 A1 Dec. 4, 2014

(30) Foreign Application Priority Data

May 31, 2013 (JP) ................................. 2013-115372

(51) Int. Cl.
*F21V 7/04* (2006.01)
*G02B 23/26* (2006.01)
*A61B 1/00* (2006.01)

(52) U.S. Cl.
CPC ............ *G02B 23/26* (2013.01); *A61B 1/00059* (2013.01); *A61B 1/00096* (2013.01)

(58) Field of Classification Search
CPC ....................................................... G02B 6/0096
USPC ............................................................ 362/551
See application file for complete search history.

(56) References Cited

U.S. PATENT DOCUMENTS

2010/0317920 A1* 12/2010 Doi et al. ....................... 600/109

FOREIGN PATENT DOCUMENTS

JP 05-146400 A 6/1993

* cited by examiner

*Primary Examiner* — Anh Mai
*Assistant Examiner* — Hana Featherly
(74) *Attorney, Agent, or Firm* — Holtz, Holtz, Goodman & Chick PC

(57) ABSTRACT

An endoscope apparatus includes a body portion having a light source portion which emits illuminating light for illuminating an object, an insertion portion through which a light guide that guides light originating in the light source portion is inserted, having a distal end portion to which a plurality of adapters are attachable, and which can emit light originating in an LED from the distal end portion, an operation portion which is connectable to the body portion and has an adapter detection section that detects a type of an adapter attached to the distal end portion, and a CPU which controls the light source portion and the LED according to the type of the detected adapter.

16 Claims, 9 Drawing Sheets

ENDOSCOPE APPARATUS HAVING FIRST AND SECOND LIGHT SOURCES AND CONTROL SECTION WHICH CONTROLS THE FIRST LIGHT AND SECOND LIGHT SOURCES ACCORDING TO A DETECTED TYPE OF ATTACHED ADAPTER

CROSS REFERENCE TO RELATED APPLICATION

This application claims benefit of Japanese Application No. 2013-115372 filed in Japan on May 31, 2013, the contents of which are incorporated by this reference.

BACKGROUND OF THE INVENTION

1. Field of the Invention

The present invention relates to an endoscope apparatus and, more particularly, to an endoscope apparatus in which an operation portion is detachable from a body portion.

2. Description of the Related Art

Endoscope apparatuses have been widely utilized in industrial and medical fields. An endoscope apparatus has an insertion portion and can insert the insertion portion into a subject and observe an inside of the subject with an image pickup apparatus provided at, e.g., a distal end portion of the insertion portion. The endoscope apparatus generally has an operation portion and a body portion, and the operation portion is connected to the body portion that is a processor apparatus by a cable.

An object to be inspected may be at a high altitude, be large, or be immovable, especially in an industrial field. For the reason, some endoscope apparatuses are portable endoscope apparatuses. A portable endoscope apparatus has an insertion portion and an operation portion which is connected to a proximal end of the insertion portion, and a display apparatus is provided at the operation portion. An inspector can insert the insertion portion into an object to be inspected and perform endoscopic inspection while viewing an endoscopic image displayed on the display apparatus provided at the operation portion.

As disclosed in Japanese Patent Application Laid-Open Publication No. 5-146400, an endoscope apparatus is proposed which is configured in consideration of portability of an endoscope such that an operation portion and an outside processor apparatus which is a body portion are separable from each other. According to the proposal, endoscopic inspection without use of the outside processor apparatus is possible, and a driving/processing unit connected to the operation portion which drives a solid image pickup device and has a video signal processing circuit is configured to be detachable from the outside processor apparatus. The operation portion not only can be used while being connected to the outside processor apparatus but also can be used as a portable endoscope apparatus in endoscopic inspection without using the outside processor apparatus when a simple light source apparatus and a monitor are connected to the operation portion.

Since a large lamp or the like can be used as a light source provided at the body portion, the endoscope apparatus with the operation portion connected to the body portion is effective when a large amount of light is required.

Some inspection places or some inspection targets may require both types of endoscope apparatuses, the portable endoscope apparatus and the normal endoscope apparatus with the operation portion and the body portion connected. For example, if inspection is possible only with the portable endoscope apparatus, endoscopic inspection is performed by using the portable endoscope apparatus. If a large amount of illuminating light is required, the operation portion and the body portion are connected, and endoscopic inspection is performed by using the light source in the body portion. That is, the portable endoscope apparatus is selected and used or the endoscope apparatus with the body portion and the operation portion connected is selected and used, according to circumstances.

SUMMARY OF THE INVENTION

An endoscope apparatus according to one aspect of the present invention includes a body portion having a first light source which emits first light as illuminating light for illuminating an object, an insertion portion through which a light guide that guides the first light originating in the first light source is inserted, having a distal end portion to which an adapter is attachable, and which can emit second light originating in a second light source from the distal end portion, an operation portion which is connectable to the body portion and has an adapter detection section that detects a type of an adapter attached to the distal end portion, and a control section which controls the first light source and the second light source according to the type of the adapter detected by the adapter detection section.

An endoscope apparatus according to one aspect of the present invention includes a body portion having a first light source which emits first light as illuminating light for illuminating an object, an insertion portion through which a light guide that guides the first light originating in the first light source is inserted, an operation portion which is connectable to the body portion and has a connection detection section that detects connection to the body portion, and a control section which controls the first light source and a second light source to turn on the first light source and emit the first light originating in the first light source from a distal end portion of the insertion portion via the light guide if connection to the body portion is detected by the connection detection section in the operation portion and to turn on the second light source and emit second light originating in the second light source from the distal end portion of the insertion portion if connection to the body portion is not detected.

DETAILED DESCRIPTION OF THE PREFERRED EMBODIMENTS

An embodiment of the present invention will be described below with reference to the drawings.

(Configuration)

Figure 1:
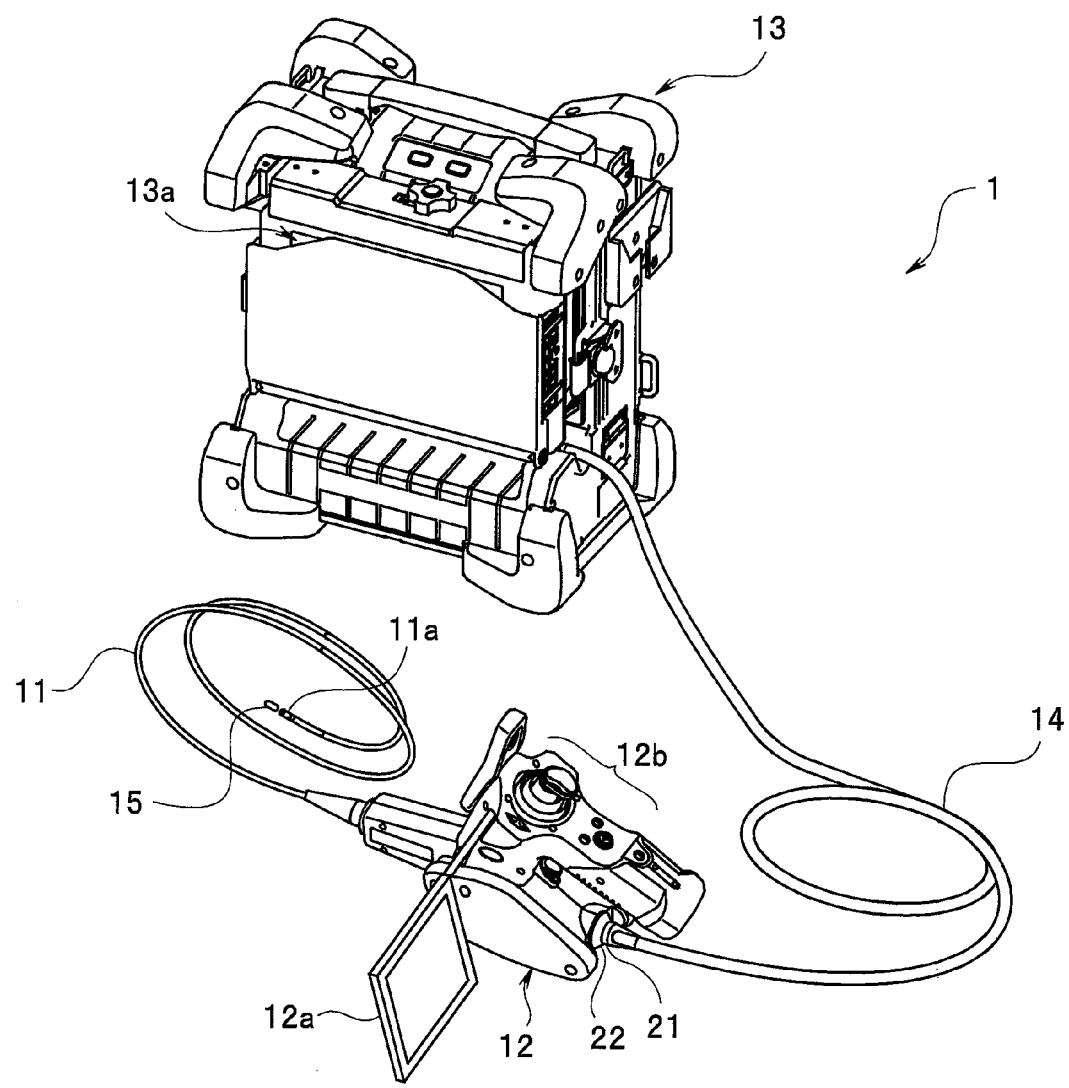
FIG. 1 is an external view of an endoscope apparatus according to an embodiment of the present invention.

FIG. 1 is an external view of an endoscope apparatus according to an embodiment of the present invention. An endoscope apparatus 1 is configured to include an operation portion 12 having an insertion portion 11 and a body portion 13. A proximal end portion of the insertion portion 11 is connected to the operation portion 12. The operation portion 12 and the body portion 13 are connected by a cable 14.

A bending portion is provided at a distal end portion 11a of the insertion portion 11. A user can easily observe an observation target while setting an image pickup direction of an image pickup device (e.g., a CCD) which is provided closer to a distal end side than the bending portion to a desired direction by bending the bending portion. An optical adapter 15 which is an adapter for an endoscope is attachable to the distal end portion 11a. In the present embodiment, the optical adapter 15 is any one of optical adapters 15A, 15B, and 15C (to be described later).

A display portion 12a and an operation device unit 12b including various buttons and a joystick are provided at the operation portion 12. A user can view an endoscopic image displayed on the display portion 12a at hand while grasping the operation portion 12 and operating the operation device unit 12b. A display portion 13a is also provided at the body portion 13. As will be described later, if the operation portion 12 is used while being connected to the body portion 13, a user can also view an endoscopic image displayed on the display portion 13a at the body portion 13. The display portions 12a and 13a are liquid crystal displays (LCDs) here. The display portion 12a is a display smaller than the display portion 13a.

A connector 21 is provided at a distal end portion of the cable 14. The connector 21 can be detachably connected to a connector 22 which is provided at the operation portion 12. That is, the operation portion 12 is connectable to the body portion 13. A signal line, a power line, and a light guide are connected to each of the connectors 21 and 22.

A user can use the operation portion 12 with the insertion portion 11 connected as an endoscope apparatus on a stand-alone basis or can use the operation portion 12 while being connected to the body portion 13, according to an environment in which the endoscope apparatus is used. That is, not only the operation portion 12 having the insertion portion 11 in the endoscope apparatus 1 can be used as an endoscope apparatus but also the endoscope apparatus 1 can be used as an endoscope apparatus composed of the operation portion 12 having the insertion portion 11 and the body portion 13. If a user uses the operation portion 12 on a stand-alone basis without connecting the operation portion 12 to the body portion 13, the user can use the operation portion 12 as a portable endoscope apparatus.

Figure 2:
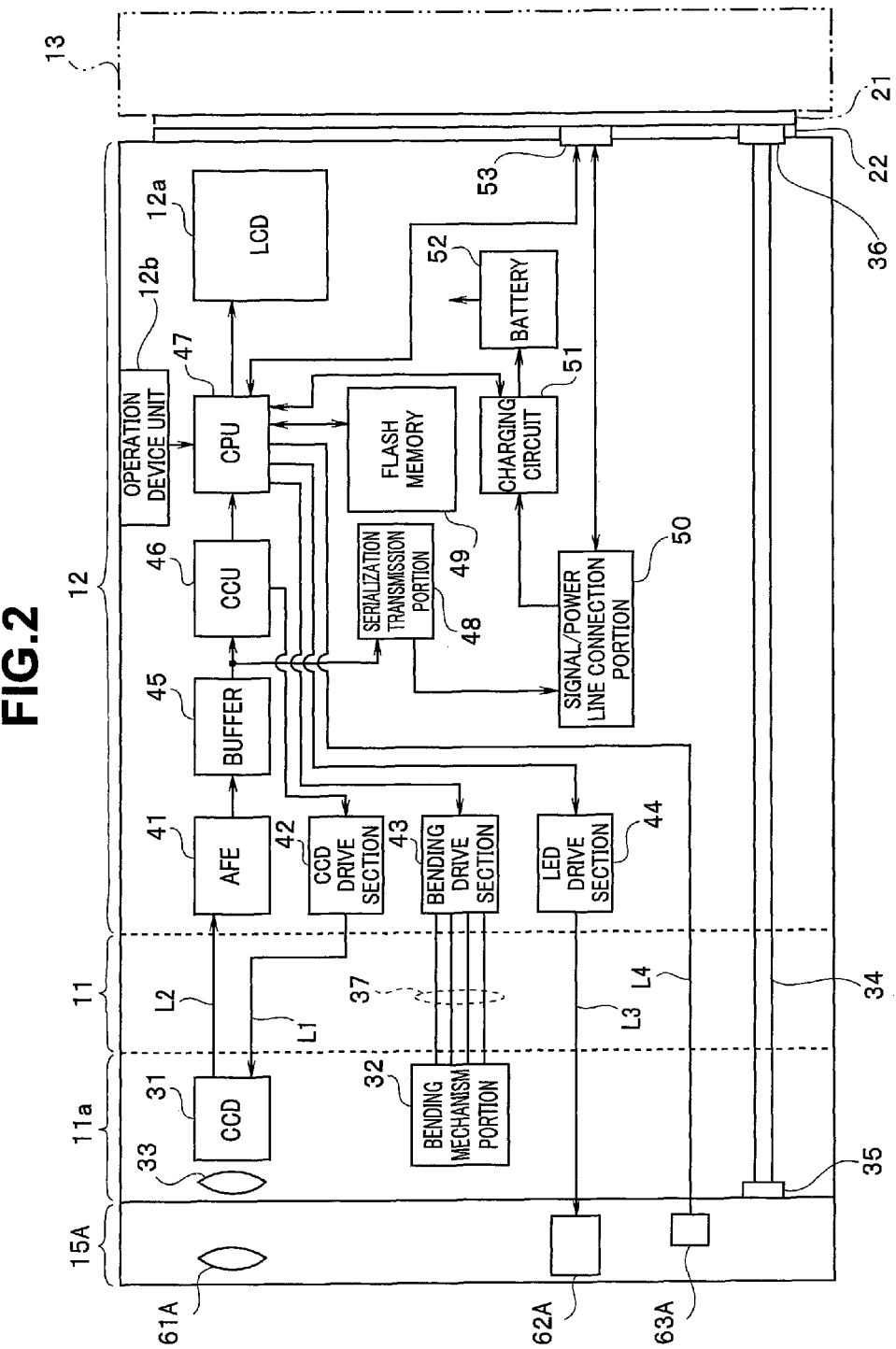
FIG. 2 is a block diagram showing a configuration when an optical adapter 15A is attached to a distal end portion 11a of an insertion portion 11, according to the embodiment of the present invention.
Figure 3:
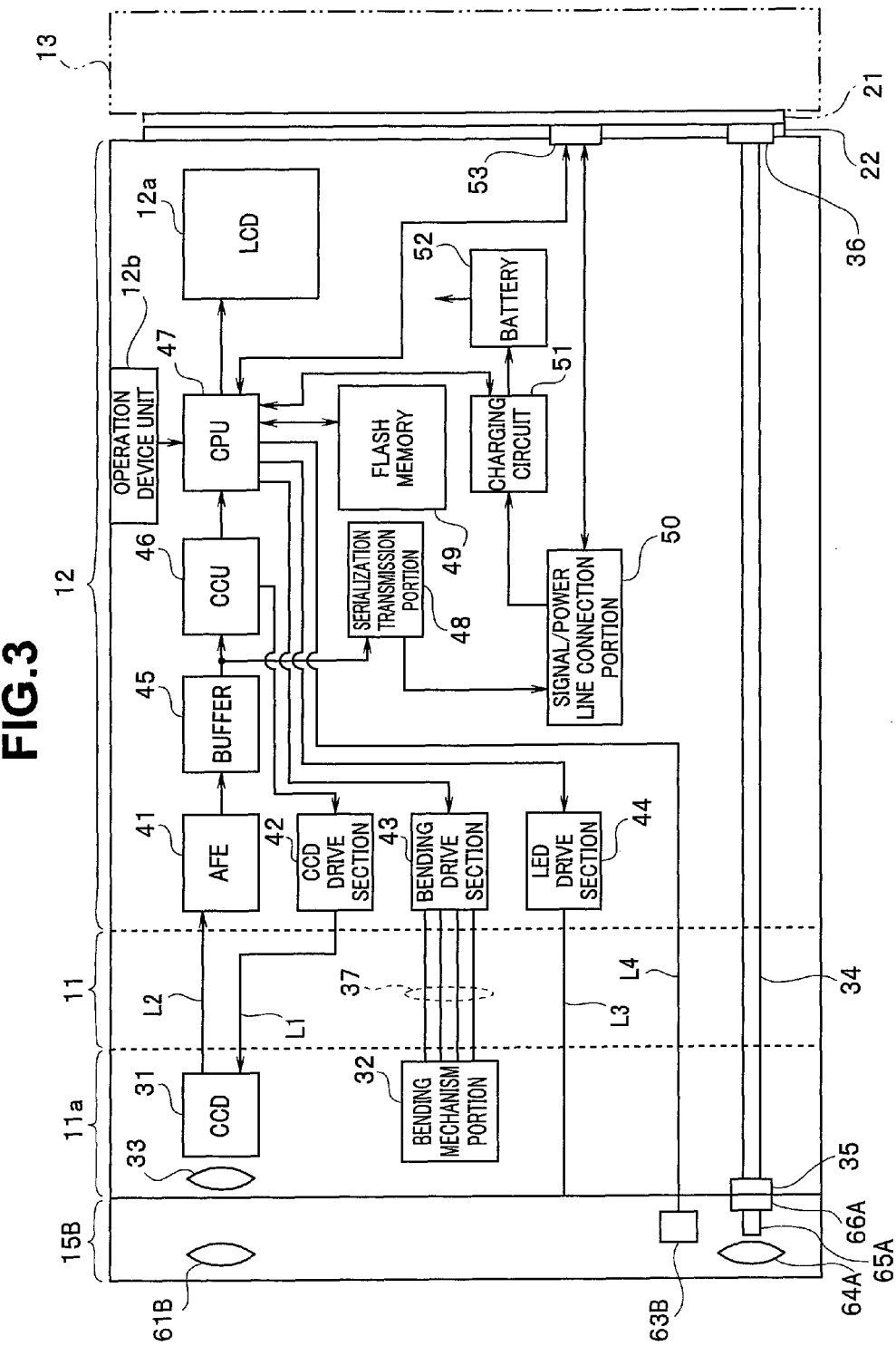
FIG. 3 is a block diagram showing a configuration when an optical adapter 15B is attached to the distal end portion 11a of the insertion portion 11, according to the embodiment of the present invention.
Figure 4:
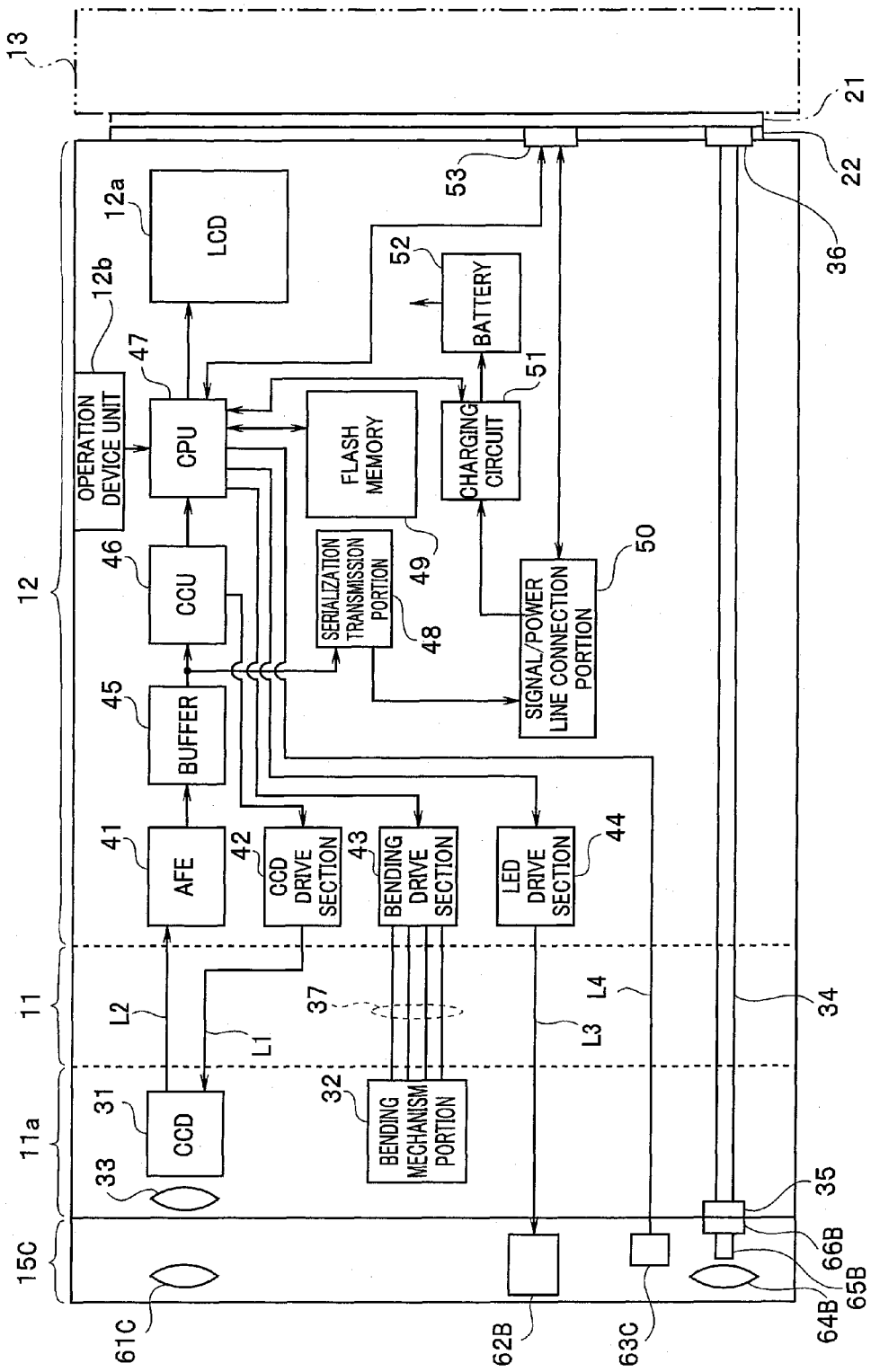
FIG. 4 is a block diagram showing a configuration when an optical adapter 15C is attached to the distal end portion 11a of the insertion portion 11, according to the embodiment of the present invention.
Figure 5:
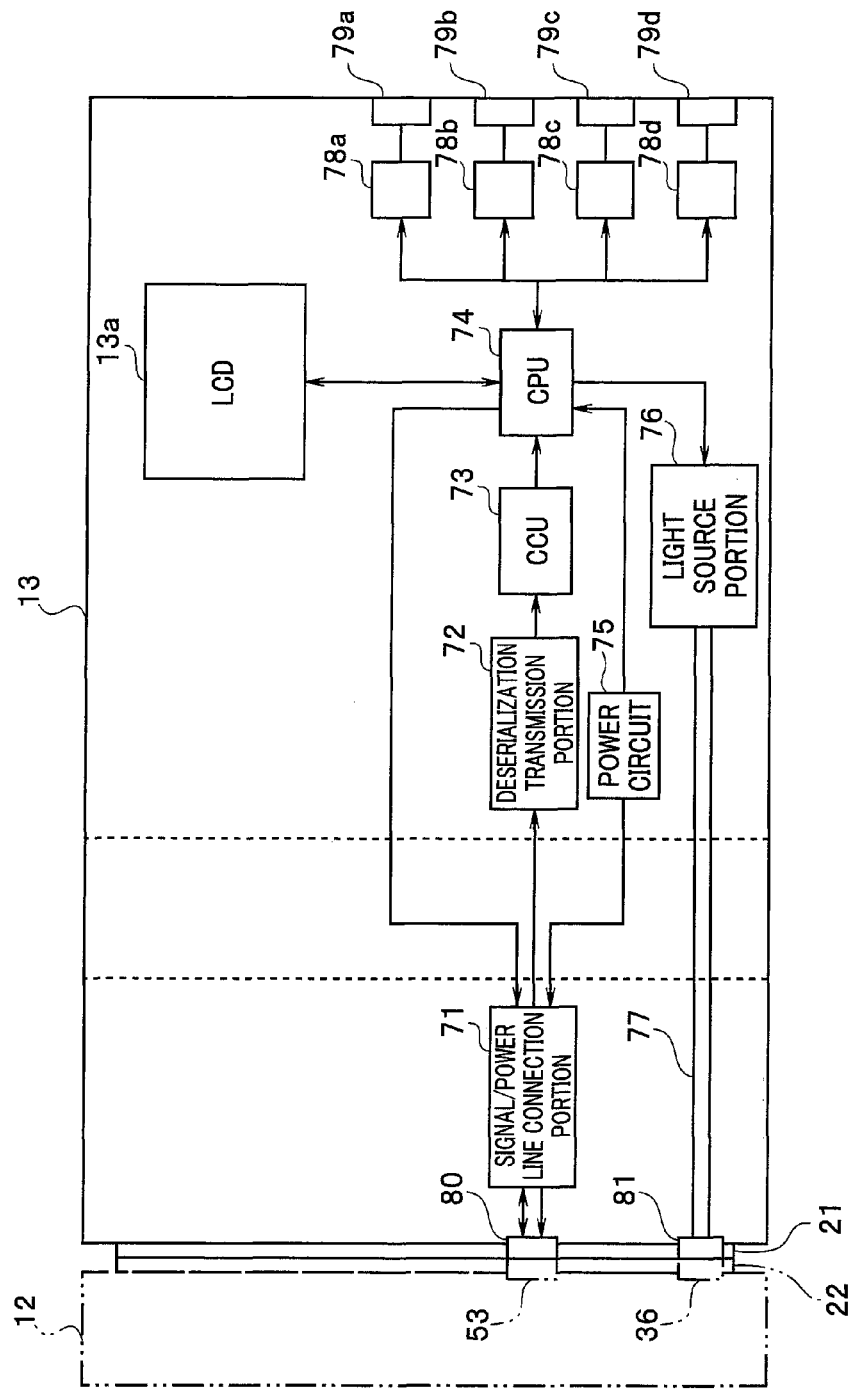
FIG. 5 is a block diagram showing an internal configuration of a body portion 13 according to the embodiment of the present invention.

FIGS. 2 to 5 are block diagrams showing an internal configuration of the endoscope apparatus 1. FIG. 2 is a block diagram showing a configuration when the optical adapter 15A is attached to the distal end portion 11a of the insertion portion 11. FIG. 3 is a block diagram showing a configuration when the optical adapter 15B is attached to the distal end portion 11a of the insertion portion 11. FIG. 4 is a block diagram showing a configuration when the optical adapter 15C is attached to the distal end portion 11a of the insertion portion 11. FIG. 5 is a block diagram showing an internal configuration of the body portion 13.

As shown in FIG. 2, if the operation portion 12 is desired to be used as a portable endoscope apparatus, a user attaches the optical adapter 15A to the distal end portion 11a of the insertion portion 11. In the case, a light-emitting diode (hereinafter referred to as an LED) 62A which is a light-emitting device as a light source provided at the optical adapter 15A serves as a light source. That is, the LED 62A is a light source which is provided at an adapter attachable to the distal end portion 11a of the insertion portion 11. Light originating in the LED 62A is illuminating light for illuminating an object.

Note that the LED 62A may be provided not at the distal end portion 11a of the insertion portion 11 but inside the operation portion 12 and that the LED 62A may emit light from the distal end portion 11a through a light guide 34 which is inserted through the insertion portion 11 or a light guide different from the light guide 34.

As shown in FIGS. 3 and 4, if the operation portion 12 is used while being connected to the body portion 13, a user attaches the optical adapter 15B or 15C to the distal end portion 11a of the insertion portion 11. In the case, a light source portion 76 (FIG. 5) which is provided inside the body portion 13 serves as the light source. The light source provided inside the body portion 13 is a light source with a large amount of light.

The optical adapter 15C for measurement includes an LED and has a light source 62B which can emit light with a predetermined pattern for measurement (e.g., a striped pattern for dimensional measurement) (see FIG. 4). That is, the LED 62B is a light source provided at an adapter attachable to the distal end portion 11a of the insertion portion 11. Light originating in the LED 62B is light for measurement.

Note that the LED 62B may be provided not at the distal end portion 11a of the insertion portion 11 but inside the operation portion 12 and that light may be emitted from the distal end portion 11a through the light guide 34 inserted through the insertion portion 11 or a light guide different from the light guide 34.

As shown in FIGS. 2, 3, and 4, a CCD 31 as an image pickup device and a bending mechanism portion 32 are provided at the distal end portion 11a of the insertion portion 11. An optical lens 33 is arranged in front of an image pickup surface of the CCD 31.

The light guide 34 is inserted through the insertion portion 11. The light guide 34 guides illuminating light from the body portion 13 to the distal end portion 11a of the insertion portion 11 when the operation portion 12 is used while being connected to the body portion 13. That is, the light guide 34 that guides light originating in the light source in the body portion 13 is inserted through the insertion portion 11.

A distal end face of the light guide 34 is fixed in close contact with a glass plate 35 which is provided at a distal end face of the distal end portion 11a of the insertion portion 11. A proximal end face of the light guide 34 is fixed in close contact with a glass plate 36 which is provided at the connector 22 of the operation portion 12. When the operation portion 12 is connected to the body portion 13, illuminating light from the body portion 13 can come incident on the proximal end face of the light guide 34, pass through the light guide 34, and exit from the distal end face of the light guide 34.

The operation portion 12 includes an analog frontend portion (hereinafter referred to as an AFE) 41, a CCD drive section 42, a bending drive section 43, an LED drive section 44, a buffer 45, a camera control unit (hereinafter referred to as a CCU) 46, a CPU 47 as a control section, the operation device unit 12b, the display portion 12a, a serialization transmission portion 48, a flash memory 49, a signal/power line connection portion 50, a charging circuit 51, and a battery 52.

The CCD 31 is connected to the CCD drive section 42 in the operation portion 12 by a signal line L1 and is driven on the basis of a driving pulse from the CCD drive section 42. The CCD drive section 42 is connected to the CPU 47 and is controlled by the CPU 47. The CCD 31 driven by the CCD drive section 42 generates an image pickup signal and outputs the image pickup signal to the AFE 41 via a signal line L2. The signal lines L1 and L2 are inserted through the insertion portion 11.

The image pickup signal is converted at the AFE 41 into a digital signal, and image data outputted from the AFE 41 is supplied to the CCU 46 via the buffer 45. The CCU 46 subjects the image data to predetermined image processing and outputs the processed image data to the CPU 47.

The CPU 47 as the control section is a microcomputer and includes a ROM and a RAM.

The operation device unit 12b is connected to the CPU 47. The operation device unit 12b includes switches for various functions, such as a freeze switch and a record switch, and the joystick for bending operation. A user can give instructions to execute a desired function by operating a desired operator.

The CPU 47 executes a predetermined process on the basis of an instruction signal from the operation device unit 12b. The CPU 47 outputs image data of a live endoscopic image to the display portion 12a on the basis of image data from the CCU 46. For example, when the freeze button is pressed, the CPU 47 acquires a still image, outputs image data of the still image to the display portion 12a, and displays the still image on the display portion 12a. When the record button is pressed, the CPU 47 encodes a still image or a movie and records the encoded still image or movie in the flash memory 49 connected to the CPU 47 or on a recording medium in the body portion 13.

If the operation portion 12 is connected to the body portion 13, the CPU 47 is connected to an electrical connection portion 53 of the connector 22 such that the CPU 47 can receive an instruction signal from the body portion 13 via the electrical connection portion 53. In the case, the CPU 47 executes processing on the basis of the instruction signal from the body portion 13.

An output of the buffer 45 branches off, and the buffer 45 is also connected to the serialization transmission portion 48. The serialization transmission portion 48 converts inputted image data from the buffer 45 into a serial signal and outputs the serial signal to the signal/power line connection portion 50.

The signal/power line connection portion 50 is a circuit for connection between a signal line which sends image data inputted from the serialization transmission portion 48 to the body portion 13 and a power line which receives power from the body portion 13. When the operation portion 12 is connected to the body portion 13, the signal/power line connection portion 50 sends image data to the body portion 13 via the electrical connection portion 53 at the connector 22.

The charging circuit 51 is connected to the signal/power line connection portion 50, and the battery 52 can be charged by the charging circuit 51. When the operation portion 12 is connected to the body portion 13, the CPU 47 detects the connection. If the operation portion 12 is connected to the body portion 13, the CPU 47 receives power from the body portion 13 via the electrical connection portion 53 at the connector 22, works the charging circuit 51 to charge the battery 52. On the other hand, if the operation portion 12 is not connected to the body portion 13, the CPU 47 stops the charging circuit 51 and drives the operation portion 12 with the battery 52.

That is, the operation portion 12 has the battery 52, and when the operation portion 12 is disconnected from the body portion 13, individual portions inside the operation portion 12 are driven with power from the battery 52 incorporated in the operation portion 12 to work. When the operation portion 12 is connected to the body portion 13, the battery 52 is charged under power supply from the body portion 13.

The bending drive section 43 is connected to the CPU 47. The bending drive section 43 includes a motor or the like and bends the bending portion of the distal end portion 11a by pulling or loosening a plurality of (four here) wires 37 which are inserted through the insertion portion 11 according to a driving control signal from the CPU 47. A user can work the bending mechanism portion 32 by operating the joystick at the operation device unit 12b and set a direction of field of view of the CCD 31 to a desired direction.

Note that the bending mechanism in the distal end portion 11a of the insertion portion 11 may not be an electric one and may be a manual one or an electrically assisted one.

The LED drive section 44 is a circuit which drives the LED 62A or 62B in the optical adapter 15A or 15C attached to the distal end portion 11a when the operation portion 12 is used on a stand-alone basis, i.e., as a portable endoscope apparatus or when the operation portion 12 is used as an endoscope apparatus for measurement. The LED drive section 44 is controlled by the CPU 47. For the reason, a signal line L3 for LED driving is inserted through the insertion portion 11, and a contact point (not shown) of the signal line L3 is provided at the distal end portion 11a. When the optical adapter 15A or 15C is attached to the distal end portion 11a, the LED drive section 44 and the LED 62A or 62B are connected via the contact point of the signal line L3.

As shown in FIG. 2, the optical adapter 15A is an LED optical adapter and has a lens 61A, the LED 62A, and an identification unit 63A.

The lens 61A is an optical member for condensing light from an object on the image pickup surface of the CCD 31 and forming an object image when the optical adapter 15A is attached to the distal end portion 11a of the insertion portion 11. Thus, when the optical adapter 15A is attached to the distal end portion 11a of the insertion portion 11, the lenses 33 and 61A constitute an objective optical system for the CCD 31.

The LED 62A constitutes a light source for illumination when the operation portion 12 is used as a portable endoscope apparatus. As described above, the CPU 47 controls the LED drive section 44 such that the LED drive section 44 supplies a best driving current for the LED 62A to emit light with a predetermined amount of light to the LED 62A via the signal line L3.

As described above, a plurality of adapters can be attached to the distal end portion 11a of the insertion portion 11 connected to the operation portion 12, and the insertion portion 11 can emit light originating in the LED 62A as a light source from the distal end portion 11a.

The identification unit 63A is a circuit for allowing the CPU 47 to identify the optical adapter 15A. The identification unit 63A is, for example, a resistor having a resistance value corresponding to the optical adapter 15A. The resistance value of the identification unit 63A is read by the CPU 47. For the reason, a signal line L4 for the identification unit 63A is inserted through the insertion portion 11, and a contact point (not shown) of the signal line L4 is provided at the distal end portion 11a. When the optical adapter 15A is attached to the distal end portion 11a, the identification unit 63A and the CPU 47 are connected via the contact point of the signal line L4.

As shown in FIG. 3, the optical adapter 15B is a light guide optical adapter and has a lens 61B, an identification unit 63B, a lens 64A, and a light guide 65A.

The lens 61B is an optical member for condensing light from an object on the image pickup surface of the CCD 31 and forming an object image when the optical adapter 15B is attached to the distal end portion 11a of the insertion portion 11, like the lens 61A.

The identification unit 63B is a circuit for allowing the CPU 47 to identify the optical adapter 15B, like the identification unit 63A. The identification unit 63B is, for example, a resistor having a resistance value corresponding to the optical adapter 15B. The resistance value of the identification unit 63B is read by the CPU 47. When the optical adapter 15B is attached to the distal end portion 11a, the identification unit 63B and the CPU 47 are connected via the contact point of the signal line L4.

The lens 64A is an optical member for emitting, to an object, light emitted from the distal end face of the light guide 34 when the optical adapter 15B is attached to the distal end portion 11a of the insertion portion 11. For the reason, the optical adapter 15B has a glass plate 66A which comes into close contact with the glass plate 35 at the distal end portion 11a when the optical adapter 15B is attached to the distal end portion 11a of the insertion portion 11. That is, light exiting from the distal end face of the light guide 34 passes through the glass plates 35 and 66A, the light guide 65A, and the lens 64A and is emitted ahead of the distal end portion 11a.

As shown in FIG. 4, the optical adapter 15C for measurement has a lens 61C, the light source 62B, an identification unit 63C, a lens 64B, and a light guide 65B.

The lens 61C is an optical member for condensing light from an object on the image pickup surface of the CCD 31 and forming an object image when the optical adapter 15C is attached to the distal end portion 11a of the insertion portion 11, like the lens 61A.

The identification unit 63C is a circuit for allowing the CPU 47 to identify the optical adapter 15C, like the identification unit 63A. The identification unit 63C is, for example, a resistor having a resistance value corresponding to the optical adapter 15C. The resistance value of the identification unit 63C is read by the CPU 47. When the optical adapter 15C is attached to the distal end portion 11a, the identification unit 63C and the CPU 47 are connected via the contact point of the signal line L4.

The lens 64B is an optical member for emitting, to an object, light emitted from the distal end face of the light guide 34 when the optical adapter 15C is attached to the distal end portion 11a of the insertion portion 11. For the reason, the optical adapter 15C has a glass plate 66B which comes into close contact with the glass plate 35 at the distal end portion 11a when the optical adapter 15C is attached to the distal end portion 11a of the insertion portion 11. That is, light exiting from the distal end face of the light guide 34 passes through the glass plates 35 and 66B, the light guide 65B, and the lens 64B and is emitted ahead of the distal end portion 11a.

As described above, the CPU 47 can determine the type of an optical adapter attached to the distal end portion 11a, i.e., whether the optical adapter is the optical adapter 15A, the optical adapter 15B, or the optical adapter 15C, on the basis of differences in resistance value among the identification units 63A, 63B, and 63C.

Note that the identification units 63A, 63B, and 63C may be not resistors but memories having respective pieces of identification data. In the case, the CPU 47 determines the type of the adapter on the basis of the pieces of identification data read out from the individual memories.

As shown in FIG. 5, the body portion 13 has a signal/power line connection portion 71, a deserialization transmission portion 72, a CCU 73, a CPU 74, the display portion 13a, a power supply circuit 75, the light source portion 76, a light guide 77, various interface circuits 78a, 78b, 78c, and 78d, and various connectors 79a, 79b, 79c, and 79d.

The signal/power line connection portion 71 is connected to the signal/power line connection portion 50 in the operation portion 12 via an electrical connection portion 80 at the connector 21 and performs reception of image data from the signal/power line connection portion 50, sending of an instruction signal from the CPU 74, and outputting of power from the power supply circuit 75.

The deserialization transmission portion 72 is a circuit which converts image data of a serial signal from the signal/power line connection portion 71 into a parallel signal and outputs the parallel signal to the CCU 73. The CCU 73 executes image processes, such as noise reduction, image rotation, and damage sensing.

Image data outputted from the CCU 73 is supplied to the CPU 74, and the CPU 74 performs measurement calculation and the like on the image data.

The CPU 74 performs overall control of the body portion 13 and outputs pieces of display data, such as an inspection image and a menu screen, to the display portion 13a.

The power supply circuit 75 generates various predetermined power voltages from an AC power source and has a battery. The power supply circuit 75 is a circuit for battery driving of the body portion 13 when the body portion 13 is not driven by the AC power source. The power supply circuit 75 is connected to the CPU 74, and the CPU 74 can recognize a driving status of the body portion 13, i.e., whether the body portion 13 is in an AC-driven state or in a battery-driven state.

The light source portion 76 incorporates a light source with a large amount of light, such as a lamp light source or a laser light source. A user can perform an inspection requiring a large amount of light, such as an inspection in a large space, by connecting the operation portion 12 to the body portion 13 and making an object sufficiently bright with use of the light source in the body portion 13. That is, the body portion 13 has a light source which emits light as illuminating light for illuminating an object.

The light source portion 76 is an apparatus which emits illuminating light under control by the CPU 74. The illuminating light is brought incident on a proximal end portion of the light guide 77 and is emitted from a distal end portion of the light guide 77. The connector 21 has a glass plate 81 which comes into close contact with the glass plate 36 at the connector 22 when the connector 22 at the operation portion 12 is connected. Thus, light emitted from a distal end face of the light guide 77 passes through the glass plates 81 and 36 and is emitted to the light guide 34 in the operation portion 12.

The display portion 13a is an LCD and has a touch panel (not shown). The CPU 74 displays various menu screens and operation screens and the like on the display portion 13a. A user can input a desired instruction to the body portion 13 to execute a desired function by touching various predetermined positions on a displayed screen.

Note that the display portion 13a may not be fixed to the body portion 13 and may be detachable. The CPU 74 outputs, to the display portion 13a, an image signal of a movie or a still image outputted from the CCU 73, and an endoscopic image is displayed on the display portion 13a.

The plurality of (four here) interface circuits (hereinafter referred to as I/Fs) 78a, 78b, 78c, and 78d are connected to the CPU 74.

The I/F 78a is an interface for a memory card and is connected to the connector 79a for a memory card. The I/F 78b is an interface for USB and is connected to the connector 79b for USB. The I/F 78c is an interface for a LAN and is connected to the connector 79c for a LAN. The I/F 78d is an interface for HDMI and is connected to the connector 79d for HDMI.

Thus, connection of an external device, such as a memory card, to a desired one of the connectors allows recording of image data of an endoscopic image as a still image or a movie on, e.g., a memory card, output of image data of an endoscopic image in HDMI format to an external video device, transfer of image data of an endoscopic image to a remote device or a remote server via a LAN, and the like.

The relatively large display portion 13a is connected to the body portion 13, which eases measurement and image processing (e.g., input of a comment) in a subsequent process and checking of an inspection image by a plurality of people.

(Action)

Working of the CPU 47 in the operation portion 12 will be described.

Figure 6:
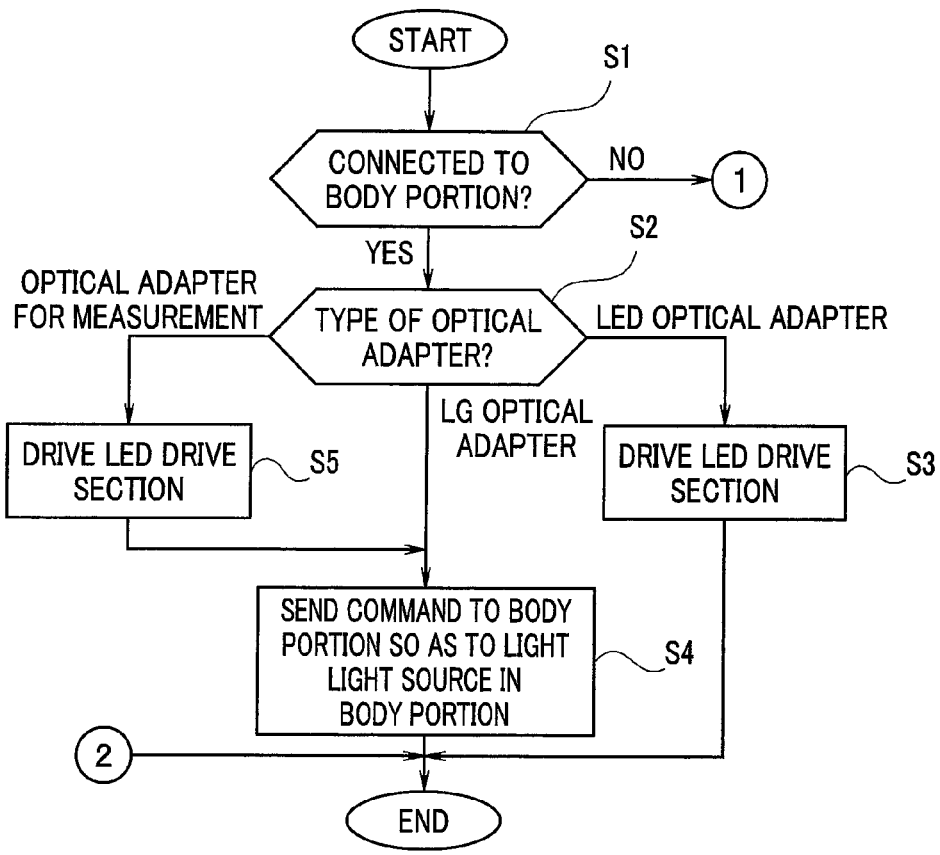
FIG. 6 is a flowchart showing an example of a flow of a process to be executed when an optical adapter is attached to the distal end portion 11a of the insertion portion 11, according to the embodiment of the present invention.
Figure 7:
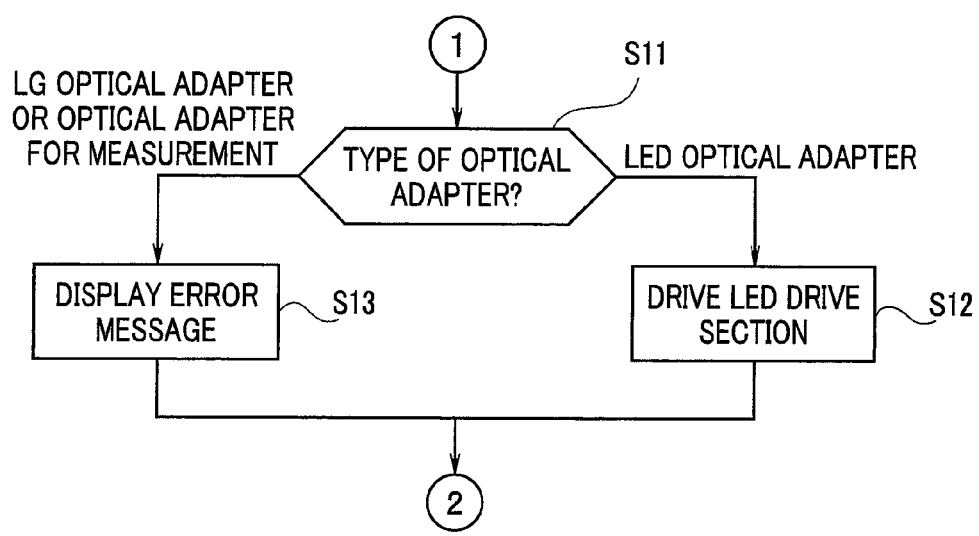
FIG. 7 is a flowchart showing the example of the flow of the process to be executed when an optical adapter is attached to the distal end portion 11a of the insertion portion 11, according to the embodiment of the present invention.

FIGS. 6 and 7 are flowcharts showing an example of a flow of a process to be executed when an optical adapter is attached to the distal end portion 11a of the insertion portion 11.

The process in FIGS. 6 and 7 is executed by the CPU 47 when the operation portion 12 is powered on while an optical adapter is attached to the distal end portion 11a.

When the operation portion 12 is powered on, the CPU 47 determines whether the operation portion 12 is connected to the body portion 13 (S1). Whether the operation portion 12 is connected to the body portion 13 can be determined through, for example, communication of the CPU 47 with the CPU 74 of the body portion 13. If communication is impossible, it is determined that the operation portion 12 is not connected to the body portion 13. The process in S1 constitutes a connection detection section which detects connection to the body portion 13, and the operation portion 12 has the connection detection section.

If the operation portion 12 is connected to the body portion 13 (YES in S1), the CPU 47 determines the type of an attached optical adapter (S2). The determination of the type of the optical adapter is made by the CPU 47 through readout of the resistance values of the identification units 63A to 63C. The process in S2 constitutes an adapter detection section which detects a type of an attached adapter, and the operation portion 12 has the adapter detection section.

If the optical adapter attached to the distal end portion 11a is the optical adapter 15A (i.e., an LED optical adapter), the CPU 47 drives the LED drive section 44 (S3). As a result, the LED 62A in the optical adapter 15A lights up.

If the optical adapter attached to the distal end portion 11a is the optical adapter 15B (i.e., an LG optical adapter), the CPU 47 sends a command to light the light source of the light source portion 76 in the body portion 13 to the body portion 13 (S4). The command is transmitted to the CPU 74 in the body portion 13 via the connectors 21 and 22. As a result, the light source portion 76 in the body portion 13 lights up, and illuminating light having passed through the light guides 77, 34, and 65A is emitted through the lens 64A in the optical adapter 15B at the distal end portion 11a.

That is, the CPU 47 as the control section controls the light source portion 76 to emit light originating in the light source portion 76 by outputting a control signal for turning on the light source portion 76 in the body portion 13 to the body portion 13, and the turning on of the light source portion 76 is performed by the body portion 13 having received the control signal.

In S3 to S5, the CPU 47 supplies information of the type of the optical adapter determined in S2 to the CPU 74 in the body portion 13 through communication. With the communication, the body portion 13 can also recognize the type of the optical adapter attached to the distal end portion 11a.

If the optical adapter attached to the distal end portion 11a is the optical adapter 15C (i.e., an optical adapter for measurement), the CPU 47 drives the LED drive section 44 (S5) and sends a command to light the light source of the light source portion 76 in the body portion 13 to the body portion 13 (S4). As a result, the LED 62B in the optical adapter 15C lights up and emits light for measurement with a predetermined pattern. The light source portion 76 in the body portion 13 also lights up, and illuminating light having passed through the light guides 77, 34, and 65B is emitted through the lens 64B in the optical adapter 15C at the distal end portion 11a.

If the operation portion 12 is not connected to the body portion 13 (NO in S1), the CPU 47 determines the type of the attached optical adapter (S11).

If the optical adapter attached to the distal end portion 11a is the optical adapter 15A (i.e., an LED optical adapter), the CPU 47 drives the LED drive section 44 (S12). As a result, the LED 62A in the optical adapter 15A lights up.

If the optical adapter attached to the distal end portion 11a is the optical adapter 15B (i.e., an LG optical adapter) or the optical adapter 15C (i.e., an optical adapter for measurement), the CPU 47 generates predetermined message data and outputs the predetermined message data to the display portion 12a such that an error message is displayed on the display portion 12a at the operation portion 12 and displays the error message (S13). As a result, a user can recognize that a wrong optical adapter is attached to the distal end portion 11a.

As described above, the CPU 47 constitutes a control section which controls the LED 62A and the light source portion 76 so as to turn on the light source portion 76 and emit light originating in the light source portion 76 from the distal end portion 11a of the insertion portion 11 via the light guide 34 when connection of the operation portion 12 to the body portion 13 is detected through the process in S1 and turn on the LED 62A and emit light originating in the LED 62A from the distal end portion 11a of the insertion portion 11 when connection to the body portion 13 is not detected.

The CPU 47 also constitutes a control section which controls the LED 62A and the light source portion 76 according to the type of an adapter detected through the process in S2.

Figure 8:
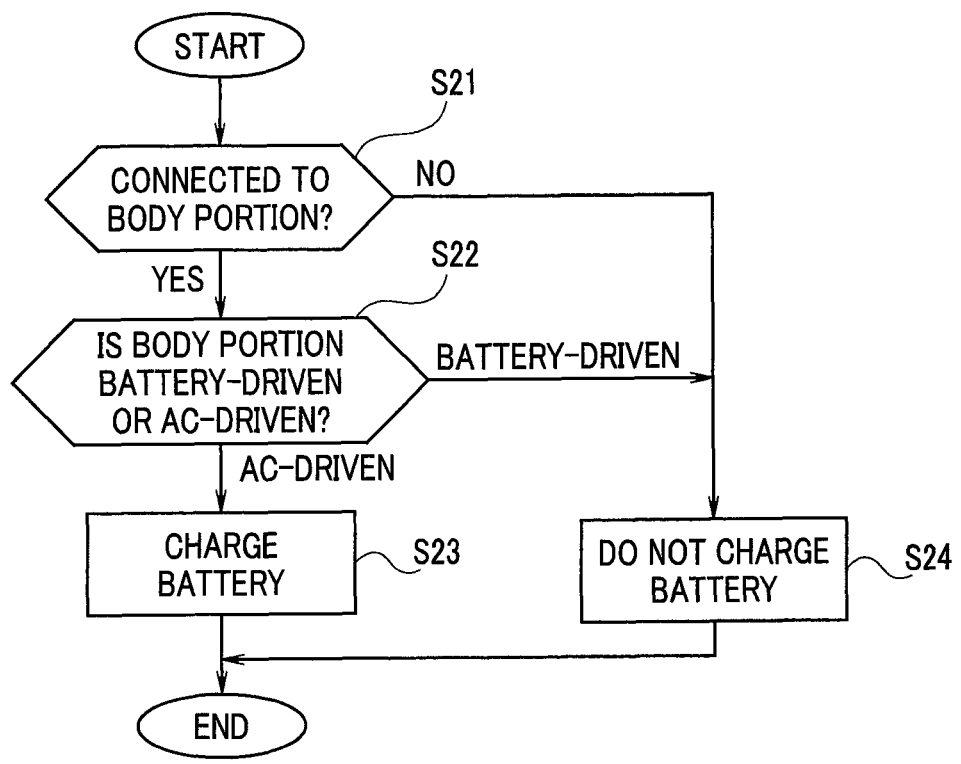
FIG. 8 is a flowchart showing an example of a flow of a battery charging control process to be executed when a status of connection between an operation portion 12 and the body portion 13 changes, according to the embodiment of the present invention.

FIG. 8 is a flowchart showing an example of a flow of a battery charging control process to be executed when a status of connection between the operation portion 12 and the body portion 13 changes.

The process in FIG. 8 is executed by the CPU 47 when a change in the status of connection to the body portion 13 is detected. The CPU 47 determines whether the operation portion 12 is connected to the body portion 13 (S21). The status of connection to the body portion 13 is detected on the basis of whether the CPU 47 is capable of communication with the CPU 74 in the body portion 13.

If the operation portion 12 is connected to the body portion 13 (YES in S21), the CPU 47 determines whether the body portion 13 is in a battery-driven state or in an AC-driven state (S22). The determination in S22 can be made by the CPU 47 through communication with the CPU 74 in the body portion 13 and reception of information of the driving status of the body portion 13 from the CPU 74.

If the body portion 13 is in an AC-driven state (YES in S22), the CPU 47 controls the charging circuit 51 to charge the battery 52 (S23). Note that, in the case, the operation portion 12 is driven not by using the battery 52 but by utilizing power from the body portion 13.

If the body portion 13 is in a battery-driven state (NO in S22) or if the operation portion 12 is not connected to the body portion 13 (NO in S21), the CPU 47 controls the charging circuit 51 not to charge the battery 52 (S24).

Figure 9:
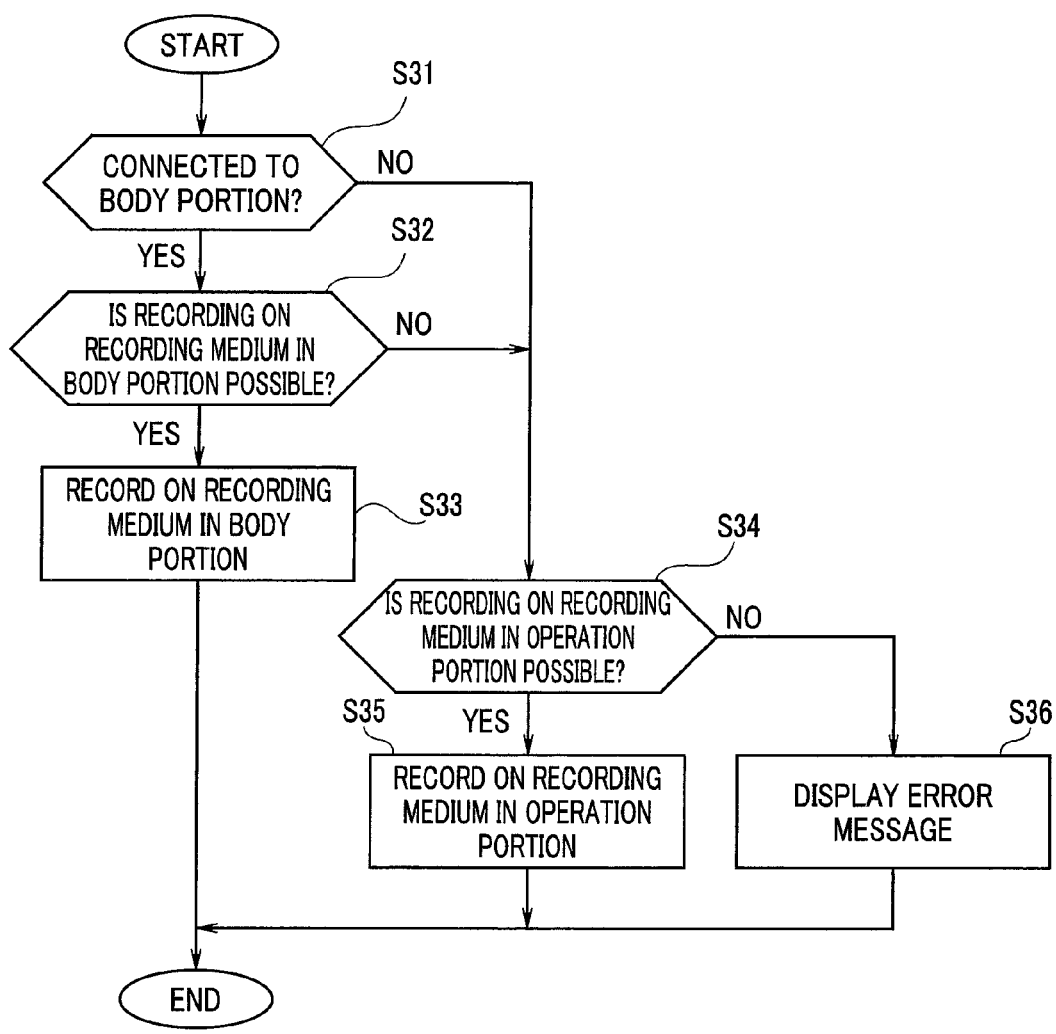
FIG. 9 is a flowchart showing an example of a flow of a recording control process to be executed when a record button at the operation portion 12 is operated, according to the embodiment of the present invention.

FIG. 9 is a flowchart showing an example of a flow of a recording control process to be executed when the record button at the operation portion 12 is operated.

The process in FIG. 9 is executed by the CPU 47 when the record button at the operation device unit 12b of the operation portion 12 is pressed.

The CPU 47 determines whether the operation portion 12 is connected to the body portion 13 (S31). If the operation portion 12 is connected to the body portion 13 (YES in S31), the CPU 47 determines whether recording in a memory card attached to the I/F 79a for a memory card or a USB memory attached to the I/F 79b for USB which is a recording medium in the body portion 13 is possible (S32). The determination can be made by the CPU 47 through communication with the CPU 74 in the body portion 13, reception of information on a free space of the recording medium in the body portion 13, and comparison of the free space with the amount of data to be recorded.

If recording on the recording medium in the body portion 13 is possible (YES in S32), i.e., the memory card or the like attached to the body portion 13 has a free space enough to record image data to be recorded, the CPU 47 sends the image data to be recorded to the CPU 74, and the image data is recorded on the recording medium in the body portion 13 (S33).

If the operation portion 12 is not connected to the body portion 13 (NO in S31) or if recording on the recording medium in the body portion 13 is not possible (NO in S32), the CPU 47 determines whether recording in the flash memory 49 that is a recording medium in the operation portion 12 is possible (S34). The determination can be made by the CPU 47 through checking of information on a free space of the flash memory 49.

If recording in the flash memory 49 is possible (YES in S34), the CPU 47 records the image data in the flash memory 49 that is the recording medium in the operation portion 12 (S35). If recording in the flash memory 49 is not possible (NO in S34), the CPU 47 generates a predetermined error message and displays the error message on the display portion 12a (S36).

Figure 10:
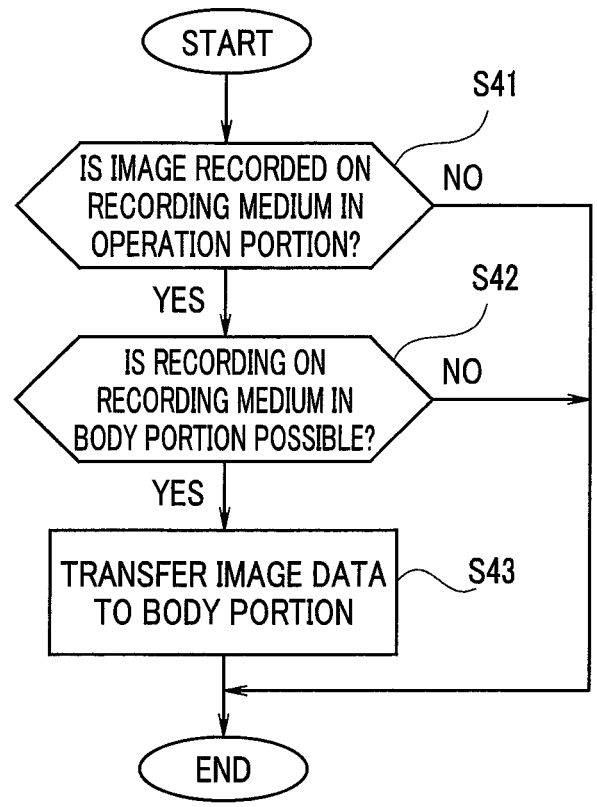
FIG. 10 is a flowchart showing an example of a flow of a transfer control process of transferring image data recorded in the operation portion 12 to the body portion 13 when the operation portion 12 is connected to the body portion 13, according to the embodiment of the present invention.

FIG. 10 is a flowchart showing an example of a flow of a transfer control process of transferring image data recorded in the operation portion 12 to the body portion 13 when the operation portion 12 is connected to the body portion 13.

The process in FIG. 10 is executed by the CPU 47 when the operation portion 12 is connected to the body portion 13 while the operation portion 12 is used singly and image data is recorded in the flash memory 49.

When the operation portion 12 is connected to the body portion 13, the CPU 47 determines whether image data is recorded in the flash memory 49 that is the recording medium in the operation portion 12 (S41). If the operation portion 12 is used singly, and image data of an endoscopic image obtained through inspection has been recorded in the flash memory 49 (YES in S41), the CPU 47 determines whether recording in a memory card attached to the I/F 79a for a memory card or a USB memory attached to the I/F 79b for USB which is a recording medium in the body portion 13 is possible (S42). The determination can be made by the CPU 47 through communication with the CPU 74 in the body portion 13, reception of the information on a free space of the recording medium in the body portion 13, and comparison of the free space with the amount of data to be recorded.

If recording on the recording medium in the body portion 13 is possible (YES in S42), the CPU 47 transfers the image data recorded in the flash memory 49 to the body portion 13 (S43).

If no image data has been recorded in the flash memory 49 (NO in S41) or if recording on the recording medium in the body portion 13 is not possible (NO in S42), the process ends without any process, i.e., without transferring image data to the body portion 13.

Note that when the operation portion 12 is disconnected from the body portion 13, the body portion 13 detects the disconnection of the operation portion 12 and turns off functions other than a function of sensing connection of the operation portion 12 (e.g., powers off the display portion 13a connected to the body portion 13 and turns off a function of the CCU 73).

When the operation portion 12 disconnected from the body portion 13 detects the disconnection, the operation portion 12 switches immediately to a battery-driven state.

When the operation portion 12 is connected to the body portion 13 again, the body portion 13 senses the connection of the operation portion 12 and turns on all functions of the body portion 13.

As described above, according to the above-described endoscope apparatus, since the operation portion 12 and the body portion 13 are both provided with a display portion, not only the operation portion 12 disconnected from the body portion 13 can be used as a stand-alone endoscope apparatus but also the operation portion 12 connected to the body portion 13 can be used as an endoscope apparatus. If the operation portion 12 and the body portion 13 are united together and are used as an endoscope apparatus, a user can easily check an inspection image on the display portion 12a at the operation portion 12 during inspection. When a plurality of people check an inspection image after inspection, when measurement processing and image processing are performed in a subsequent process after inspection, or in other cases, work can be smoothly performed by using the large display portion 13a at the body portion 13.

Note that although the type of an adapter is detected, and light source control, i.e., whether the light source in the operation portion 12 is used, the light source in the body portion 13 is used, or both the light sources are used is selected according to the type of the adapter in the above-described example, the light source control, i.e., whether the light source in the operation portion 12 is used or the light source in the body portion 13 is used may be selected according to whether the operation portion 12 is connected to the body portion 13.

For example, when the operation portion 12 is connected to the body portion 13, the CPU 47 controls the LED 62A and the light source portion 76 to turn off the LED 62A and turn on the light source portion 76 such that light originating in the light source portion 76 in the body portion 13 is used as illuminating light. On the other hand, when the operation portion 12 is not connected to the body portion 13, the CPU 47 controls the LED 62A and the light source portion 76 to turn on the LED 62A and turn off the light source portion 76 such that light originating in the LED 62A is used as illuminating light.

As described above, according to the above-described embodiment, an endoscope apparatus in which an operation portion is removable from a body portion and can be used singly can be provided, and the endoscope does not require complicated work and can be used both in a form in which the operation portion is used singly and in a form in which the body portion and the operation portion are connected.

The present invention is not limited to the embodiment, and various changes, alterations, and the like can be made without departing from the scope of the present invention.

What is claimed is:

1. An endoscope apparatus comprising:
a body portion having a first light emitting device which emits first light as illuminating light for illuminating an object;
an insertion portion through which a light guide that guides the first light originating in the first light emitting device is inserted, having a distal end portion to which an adapter is attachable, and which can emit second light originating in a second light emitting device from the distal end portion;
an operation portion which is connectable to the body portion and has an adapter detection section that detects a type of an adapter attached to the distal end portion; and
a control section which controls the first light emitting device and the second light emitting device according to the type of the adapter detected by the adapter detection section.

2. The endoscope apparatus according to claim 1, wherein:
the second light emitting device is provided at an adapter which is attachable to the distal end portion of the insertion portion.

3. The endoscope apparatus according to claim 1, wherein:
the second light originating in the second light emitting device is the illuminating light for illuminating the object.

4. The endoscope apparatus according to claim 1, wherein:
the second light originating in the second light emitting device is light for measurement.

5. The endoscope apparatus according to claim 1, wherein:
the second light emitting device is provided at the operation portion.

6. The endoscope apparatus according to claim 5, wherein:
the second light originating in the second light emitting device is the illuminating light for illuminating the object.

7. The endoscope apparatus according to claim 5, wherein:
the second light originating in the second light emitting device is light for measurement.

8. The endoscope apparatus according to claim 1, wherein:
the control section controls the first light emitting device by outputting a control signal for turning on the first light emitting device to the body portion such that the first light emitting device emits the first light, and
the turning on of the first light emitting device is performed by a control section in the body portion that receives the control signal.

9. An endoscope apparatus comprising:
a body portion having a first light emitting device which emits first light as illuminating light for illuminating an object;
an insertion portion through which a light guide that guides the first light originating in the first light emitting device is inserted;
an operation portion which is connectable to the body portion and has a connection detection section that detects connection to the body portion; and
a control section which controls the first light emitting device and a second light emitting device to turn on the first light emitting device and emit the first light originating in the first light emitting device from a distal end portion of the insertion portion via the light guide if connection to the body portion is detected by the connection detection section in the operation portion and to turn on the second light emitting device and emit second light originating in the second light emitting device from the distal end portion of the insertion portion if connection to the body portion is not detected.

10. The endoscope apparatus according to claim 9, wherein:
the second light emitting device is provided at an adapter which is attachable to the distal end portion of the insertion portion.

11. The endoscope apparatus according to claim 9, wherein:
the second light originating in the second light emitting device is the illuminating light for illuminating the object.

12. The endoscope apparatus according to claim 9, wherein:
the second light originating in the second light emitting device is light for measurement.

13. The endoscope apparatus according to claim 9, wherein:
the second light emitting device is provided at the operation portion.

14. The endoscope apparatus according to claim 13, wherein:
the second light originating in the second light emitting device is the illuminating light for illuminating the object.

15. The endoscope apparatus according to claim 13, wherein:
the second light originating in the second light emitting device is light for measurement.

16. The endoscope apparatus according to claim 9, wherein:
the control section controls the first light source by outputting a control signal for turning on the first light emitting device to the body portion such that the first light emitting device emits the first light, and
the turning on of the first light emitting device is performed by a control section in the body portion that receives the control signal.

* * * * *